US00PP36323P2

(12) United States Plant Patent
Ranney et al.

(10) Patent No.: US PP36,323 P2
(45) Date of Patent: Dec. 17, 2024

(54) ***RHODODENDRON* PLANT NAMED 'NCRX12'**

(50) Latin Name: ***Rhododendron* hybrid**
Varietal Denomination: NCRX12

(71) Applicant: North Carolina State University, Raleigh, NC (US)

(72) Inventors: Thomas Green Ranney, Arden, NC (US); Irene Palmer, Arden, NC (US); Nathan Lynch, Arden, NC (US); Andra Windorf Nus, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/745,832

(22) Filed: Jun. 17, 2024

(51) Int. Cl.
*A01H 5/02* (2018.01)
*A01H 6/36* (2018.01)

(52) U.S. Cl.
USPC ..... Plt./240
CPC ..... *A01H 6/364* (2018.05)

(58) Field of Classification Search
USPC ..... Plt./240, 239
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Rhododendron* plant named 'NCRX12' is disclosed, characterized by a floriferous plant with a prostrate, compact habit. Single deep-pink flowers bloom in spring and rebloom in fall. The new variety is a *Rhododendron,* normally produced as an outdoor garden or container plant.

2 Drawing Sheets

Latin name of the genus and species: *Rhododendron* hybrid.

Variety denomination: 'NCRX12'.

BACKGROUND OF THE INVENTION

The present invention comprises a new and distinct hybrid evergreen *Azalea* cultivar hereinafter referred to by the cultivar name 'NCRX12'. This hybrid *Azalea* was developed by a controlled breeding program at a research nursery in Mills River, North Carolina. 'NCRX12' was selected from a population of plants derived from the controlled, hand pollination of an emasculated female hybrid 'Cherry Drops', unpatented, and male parent, experimental hybrid 'H2009-266-052', unpatented. 'NCRX12' was selected from this population of seedlings after 5 years in trials. Container trials were conducted using pine bark media supplemented with 1.04 kg·m-3 dolomitic lime, 0.74 kg·m-3 granulated micronutrients and top-dressed with 5-to 6-month slow-release fertilizer. Full-sun field trials were conducted in plastic-covered, bark-amended clay soils with minimum winter temperatures of −2° F. (−19° C.) and maximum summer temperatures 98° F. (37° C.). The new cultivar 'NCRX12' was found and selected in 2013.

The first asexual propagation of 'NCRX12' occurred in 2015 by rooting stem cuttings at the same research nursery in Mills River, North Carolina. 'NCRX12' roots readily from firm softwood cuttings treated with a basal dip of 3,000 ppm indole butyric acid (potassium salt) in water. 'NCRX12' has been found to retain its distinctive characteristics through successive asexual propagations over 8 years.

Date of first public exposure was on Jun. 27, 2023, in the United States. This was made directly by the inventor or one who obtained the claimed invention directly or indirectly from the inventor. This disclosure and all public disclosures made between Jun. 27, 2023, and the filing of this application fall within the exception allowed under 102 (b) (1).

SUMMARY OF THE INVENTION

The cultivar 'NCRX12' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCRX12.' These characteristics in combination distinguish 'NCRX12' as a new and distinct *Rhododendron* cultivar:

1. Floriferous spring flower display.
2. Single deep pink flowers.
3. Prostrate, compact habit.
4. Consistent fall reblooming.

PARENT COMPARISONS

Plants of the new cultivar 'NCRX12' are similar to plants of the seed parent in most horticultural characteristics. However, plants of the new cultivar 'NCRX12' differ in the following:

1. Flowers of the new variety are a dark, fuchsia pink, while flowers of the seed parent are bright red-pink.

Plants of the new cultivar 'NCRX12' could not be compared to plants of the pollen parent as there is no record of its traits.

COMMERCIAL COMPARISONS

'NCRX12' can be compared to the commercial variety *Rhododendron* 'Conled', U.S. Plant Pat. No. 10,568. Plants of the new variety are similar to 'Conled' in most horticultural characteristics, however, 'NCRX12' differs in the following:

1. Flower color of the new variety is a deeper pink than flower color of this comparator.
2. Flowers of the new variety are smaller than flowers of this comparator.
3. Growth habit of the new variety is prostrate, while the growth habit of this comparator is globose.
4. Mature plants of the new variety are smaller than mature plants of this comparator.

'NCRX12' can be compared to the commercial variety *Rhododendron* 'NCRX11', U.S. Plant Pat. No. 35,082. Plants of the new variety are similar to 'NCRX11' in most horticultural characteristics, however, 'NCRX12' differs in the following:

1. Flower color of the new variety is a deeper pink than the flower color of this comparator.
2. Flowers of the new variety are single, while flowers of this comparator are semi-double to double.

BRIEF DESCRIPTION OF THE PHOTOGRAPHS

The accompanying photographs were taken using conventional techniques and although colors may appear different from actual colors due to light reflectance it is as accurate as possible by conventional photographic techniques.

DETAILED BOTANICAL DESCRIPTION

Figure 1:
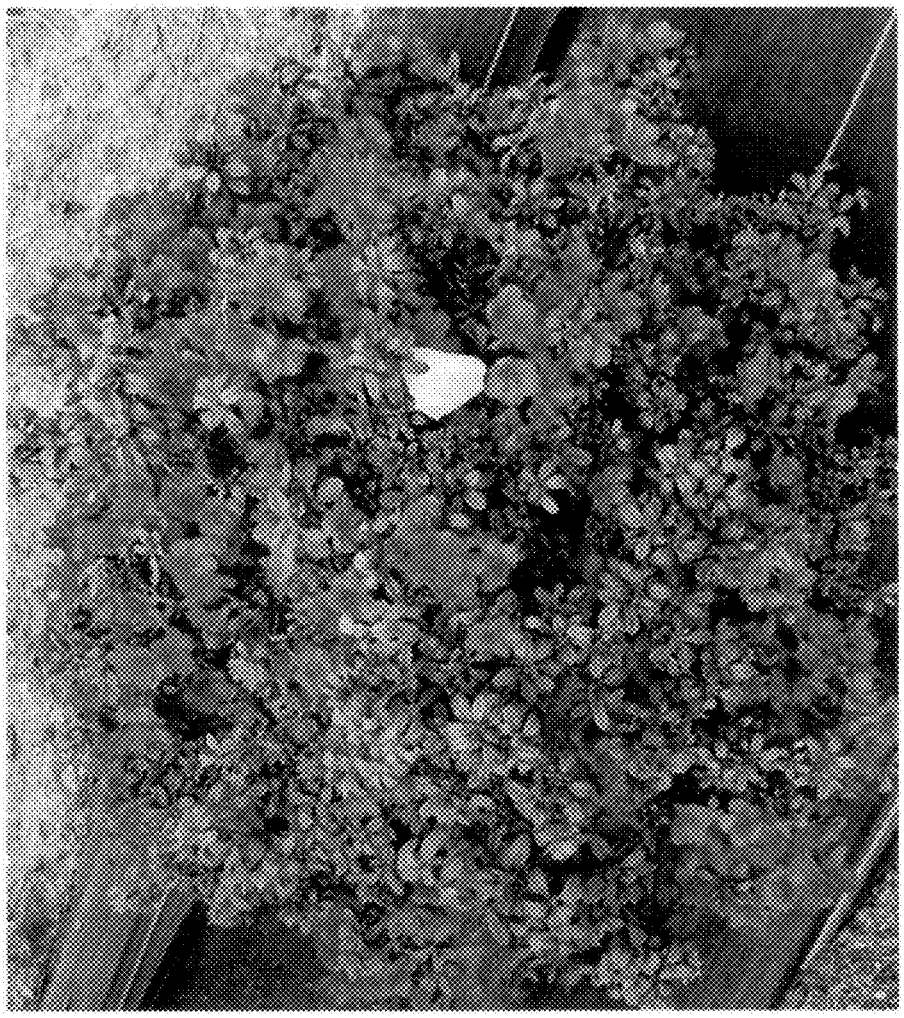
FIG. 1 is a photograph of the habit of a four-year-old field-grown plant of 'NCRX12' in Mills River, NC in spring 2019.
Figure 2:
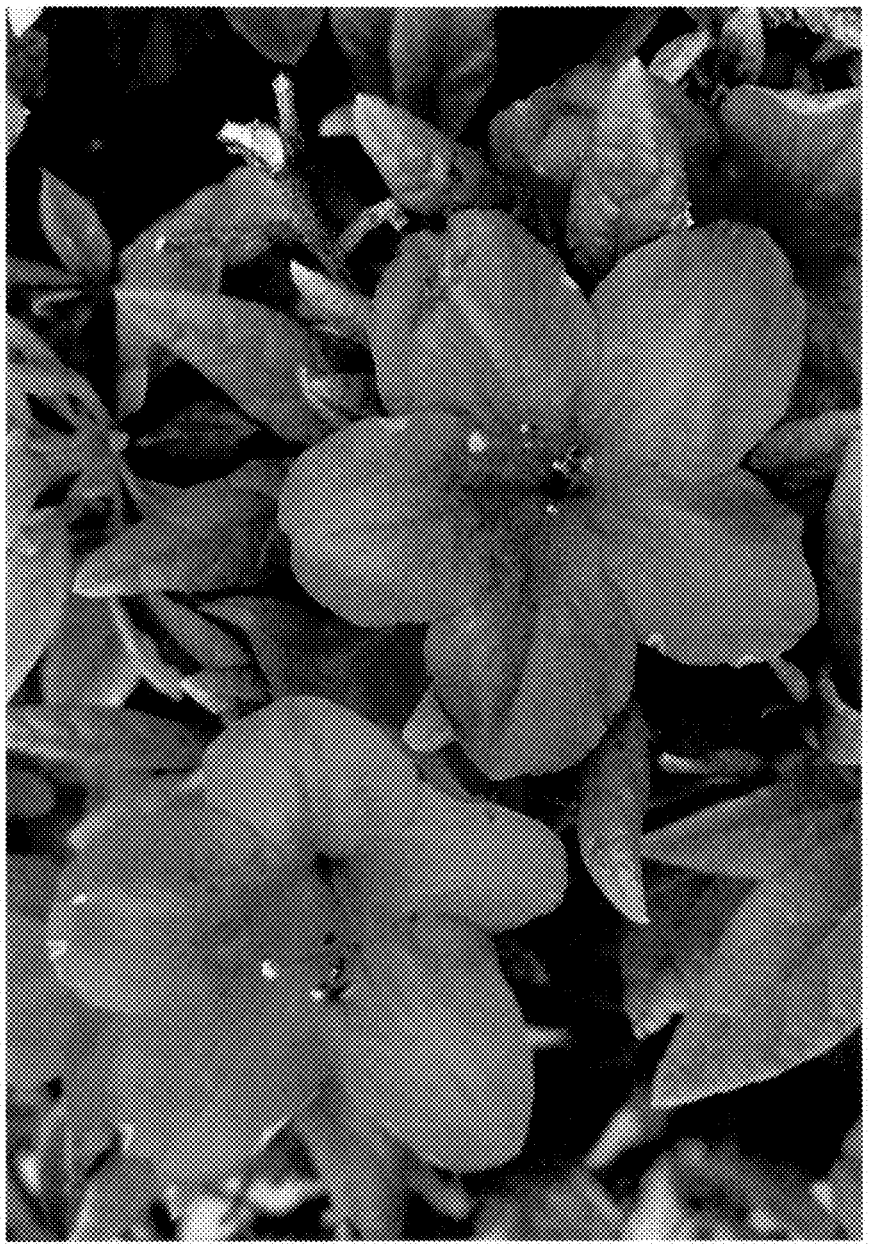
FIG. 2 is a photograph of the deep pink flowers of a three-year-old container-grown plant of 'NCRX12' in Mills River, NC in spring 2023.

The following is a detailed description of the botanical characteristics of the new and distinct *Rhododendron* 'NCRX12'. The detailed description was taken from a three-year-old, container-grown plant, in Mills River, North Carolina in 2023. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Rhododendron* hybrid 'NCRX12'.

PROPAGATION

Method: Softwood cuttings.
Time to initiate roots: 60 days at 18° to 27° C. in summer.
Time to produce rooted young plant: 80 days in summer.
Root description: Dense, freely branched, thin to medium thickness, and fibrous. White to brown in color, not accurately measured using R.H.S. chart.

PLANT

Age of plant described: 3 years old.
Growth habit: Prostrate, compact.
Height: 30 cm.
Plant spread: 50 cm.
Branches (woody branches 2 years and older):
- *Length*.—About 17 cm.
- *Diameter*.—About 0.5 cm.
- *Color*.—RHS Brown N199B.
- *Texture*.—Pubescent.

Shoots (current year's growth):
- *Length*.—About 17 cm.
- *Diameter*.—About 0.2 cm.
- *Color*.—RHS Yellow-Green N144D.
- *Texture*.—Pubescent.

Shoots (prior year's growth):
- *Length*.—About 17 cm.
- *Diameter*.—About 0.3 cm.
- *Color*.—RHS Greyed-Orange 165A.
- *Texture*.—Pubescent.

Internode length: Average 1 cm.

FOLIAGE

Leaf:
- *Arrangement*.—Alternate, simple.
- *Persistence*.—Evergreen.
- *Length*.—Average 2.2 cm.
- *Width*.—Average 1 cm.
- *Shape*.—Ovate.
- *Apex*.—Mucronate.
- *Base*.—Cuneate.
- *Margin*.—Entire.
- *Texture*.—Top surface: Pubescent. Bottom surface: Pubescent.
- *Color*.—Young foliage upper side: RHS Green 138A. Young foliage under side: RHS Yellow-Green 146B. Mature foliage upper side: RHS Green NN137A. Mature foliage under side: RHS Yellow-Green 147B. Fall foliage upper side: RHS Green NN137A. Fall foliage under side: RHS Yellow-Green 147B.
- *Venation*.—Type: Reticulate.
- *Petiole*.—Length: About 0.4 cm. Diameter: About 0.1 cm. Texture: Both sides pubescent. Color: RHS Yellow-Green 146C.

FLOWER

Natural flowering season: April to May, reblooms late September through October, in Mills River, NC.
Inflorescence type: Congested terminal raceme (truss).
Quantity of flowers: 1 to 5 per truss.
Lastingness of flowers: Each flower lasts approximately 3-7 days.
Fragrance: None.
Persistence: Self-cleaning.
Truss bud:
- *Length*.—About 1.2 cm.
- *Diameter*.—About 0.6 cm.

Bud scales:
- *Number*.—5 to 8.
- *Length*.—Average 0.7 cm.
- *Width*.—Average 0.5 cm.
- *Color*.—RHS Yellow-Green 145B.
- *Texture*.—Pubescent.

Perianth:
- *Shape*.—Funnel shaped.
- *Height*.—Average 2.6 cm.
- *Diameter at anthesis*.—Average. 4.0 cm.
- *Arrangement*.—Whorled.
- *Aspect*.—Facing upwards and outwards.
- *Attachment*.—Pedicellate.

Petals:
*Number.*—5.
*Length.*—Average 3 cm.
*Width.*—Average 1.7 cm.
*Shape.*—Obovate.
*Apex.*—Obtuse.
*Base.*—Fused.
*Margin.*—Entire.
*Texture, upper and lower surfaces.*—Glabrous.
*Color.*—Color is consistent from opening to anthesis. When opening, inner side: RHS Purple-Red 61C. When opening, outer side: RHS Purple-Red 61C. Blotch: None.

Sepals:
*Number.*—5.
*Length.*—About 0.7 cm.
*Width.*—About 0.3 cm.
*Shape.*—Lanceolate.
*Apex.*—Cuneate.
*Base.*—Truncate.
*Margin.*—Ciliate.
*Texture, upper and lower surfaces.*—Pubescent.
*Color* (*both surfaces*).—RHS Yellow-Green 146D.

Pedicels:
*Length.*—Average 0.8 cm.
*Diameter.*—About 0.1 cm.
*Color.*—RHS Yellow-Green RHS 146D.
*Texture.*—Pubescent.

REPRODUCTIVE ORGANS

Gynoecium:
*Pistil number.*—1.
*Pistil length.*—About 2.8 cm.
*Style length.*—About 2.4 cm.
*Style width.*—About 0.1 cm.
*Style color.*—RHS Purple-Red 61B.
*Stigma shape.*—Orbicular.
*Stigma length.*—About 0.1 cm.
*Stigma width.*—About 0.1 cm.
*Ovary shape.*—Orbicular.
*Ovary length.*—0.4 cm.
*Ovary diameter.*—0.3 cm.
*Ovary texture.*—Pubescent.
*Ovary color.*—RHS Yellow-Green 145A.

Androecium:
*Stamen number.*—5.
*Anther shape.*—Ovoid with two apical pores.
*Anther attachment.*—Dorsifixed.
*Anther length.*—About 0.1 cm.
*Anther width.*—About 0.1 cm.
*Filament length.*—About 2.5 cm.
*Filament diameter.*—Less than 0.1 cm.
*Filament color.*—RHS Purple-Red 61C.
*Amount of pollen.*—Normal.
*Pollen type.*—Thread-like. Pollen Color: RHS White NN155C.

OTHER CHARACTERISTICS

Fruit and seed: None observed.
Disease/pest resistance: Neither resistance nor susceptibility to the normal pests and diseases of *Rhododendron* has been observed.
Cold hardiness: Reliably cold-hardy in USDA zone 6b.

What is claimed is:

1. A new and distinct cultivar of *Rhododendron* plant named 'NCRX12' as illustrated and described herein.

* * * * *